United States Patent
Braun et al.

(10) Patent No.: US 10,227,621 B2
(45) Date of Patent: Mar. 12, 2019

(54) METHOD FOR PREPARING AN AQUEOUS ACRYLAMIDE SOLUTION HAVING A LOW ACRYLIC ACID CONCENTRATION

(71) Applicant: BASF SE, Ludwigshafen (DE)

(72) Inventors: Michael Guenter Braun, Heidelberg (DE); Juergen Daeuwel, Heidelberg (DE); Hans-Juergen Lang, Dudenhofen (DE); Peter Oedman, Neustadt (DE); Kai-Uwe Baldenius, Mannheim (DE); Matthias Kleiner, Goennheim (DE); Michael Kiefer, Boehl-Iggelheim (DE); Stephan Freyer, Neustadt (DE); Michael Budde, Ilvesheim (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 15/514,321

(22) PCT Filed: Sep. 30, 2015

(86) PCT No.: PCT/EP2015/072508
§ 371 (c)(1),
(2) Date: Mar. 24, 2017

(87) PCT Pub. No.: WO2016/050818
PCT Pub. Date: Apr. 7, 2016

(65) Prior Publication Data
US 2017/0283840 A1    Oct. 5, 2017

(30) Foreign Application Priority Data

Sep. 30, 2014 (EP) .................................. 14003377

(51) Int. Cl.
| | | |
|---|---|---|
| C12P 13/02 | (2006.01) | |
| C08F 20/56 | (2006.01) | |
| C07C 233/09 | (2006.01) | |
| C08L 33/26 | (2006.01) | |
| C09K 8/588 | (2006.01) | |
| D21H 17/37 | (2006.01) | |

(52) U.S. Cl.
CPC ............ *C12P 13/02* (2013.01); *C07C 233/09* (2013.01); *C08F 20/56* (2013.01); *C08L 33/26* (2013.01); *C09K 8/588* (2013.01); *C12Y 402/01084* (2013.01); *D21H 17/375* (2013.01); *C08L 2201/54* (2013.01)

(58) Field of Classification Search
CPC ... C12Y 402/01084; C08F 20/56; C12P 13/02
USPC ....................................................... 507/225
See application file for complete search history.

(56) References Cited

U.S. PATENT DOCUMENTS

| | | | |
|---|---|---|---|
| 3,597,481 A | 8/1971 | Tefertiller et al. | |
| 4,048,226 A | 9/1977 | Barber et al. | |
| 4,711,955 A | 12/1987 | Ward et al. | |
| 5,179,014 A * | 1/1993 | Watanabe ................ | C12P 13/02 435/128 |
| 5,525,711 A | 6/1996 | Hawkins et al. | |
| 5,792,608 A | 8/1998 | Swaminathan et al. | |
| 6,153,415 A * | 11/2000 | Oriel ........................ | C12N 9/80 435/129 |
| 7,129,217 B2 * | 10/2006 | Murao ..................... | C08F 20/56 514/23 |
| 2004/0175809 A1 * | 9/2004 | Peterson ................. | C12M 47/02 435/128 |
| 2007/0077634 A1 * | 4/2007 | Hughes ..................... | C12N 1/04 435/129 |
| 2007/0184536 A1 * | 8/2007 | Greenhalgh .............. | C12P 7/40 435/129 |
| 2011/0104690 A1 | 5/2011 | Yu et al. | |
| 2012/0108471 A1 * | 5/2012 | Amanullah ............ | C09K 8/145 507/104 |
| 2014/0187818 A1 * | 7/2014 | Kozulin ................... | C12N 1/20 564/204 |

FOREIGN PATENT DOCUMENTS

| | | | |
|---|---|---|---|
| EP | 0 302 175 A2 | 2/1989 | |
| FR | 2 835 531 A1 | 8/2003 | |
| WO | WO-03066800 A2 * | 8/2003 | ............... C12N 1/20 |

OTHER PUBLICATIONS

Machine translation of WO03/066800A2. (Year: 2003).*
International Search Report dated Dec. 22, 2015 in PCT/EP2015/072508 filed Sep. 30, 2015.
Written Opinion dated Dec. 22, 2015 in PCT/EP2015/072508 filed Sep. 30, 2015.
Laura Cantarella, et al., "Nitrile, amide and temperature effects on amidase-kinetics during acrylonitrile bioconversion by nitrile-hyratase/amidase in situ cascade system" Bioresource Technology, vol. 142, XP028576173, 2013, pp. 320-328.
Yuchao Ma, et al., "Identification of nitrile hydratase-producing *Rhodococcus ruber* TH and characterization of an amiE-negative mutant" Bioresource Technology, vol. 101, XP0026624004, 2010, pp. 285-291.
Marius Tudorascu, et al., "A New Process for Acrylamide Synthesis by Enzymatic Hydrolysis of Acrylonitrile in Disperse System" Revista de Chimie (Bucarest), vol. 60, No. 2, XP002752188, 2009, pp. 197-200.

* cited by examiner

*Primary Examiner* — Aiqun Li
(74) *Attorney, Agent, or Firm* — Oblon, McClelland, Maier & Neustadt L L P

(57) ABSTRACT

The present invention relates to methods for preparing an aqueous acrylamide solution having a low acrylic acid concentration. In addition, the present invention relates to methods for reducing the acrylic acid concentration of an aqueous acrylamide solution. The methods involve a bioconversion of acrylonitrile to acrylamide in the presence of a biocatalyst, wherein during the bioconversion the content of acrylonitrile is maintained at 0.3 w/w % or more referred to the total weight of the composition in the reactor. Also provided is an aqueous acrylamide solution which is obtained by the methods of the present invention. Furthermore, the present invention is related to an acrylamide homopolymer or copolymer obtained by polymerizing the acrylamide of the aqueous solution.

29 Claims, No Drawings
Specification includes a Sequence Listing.

SEQUENCE LISTING

<160> NUMBER OF SEQ ID NOS: 4

<210> SEQ ID NO 1
<211> LENGTH: 612
<212> TYPE: DNA
<213> ORGANISM: Rhodococcus rhodochrous
<220> FEATURE:
<223> OTHER INFORMATION: alpha-subunit of nitrile hydratase of
      Rhodococcus rhodochrous

<400> SEQUENCE: 1

| | | | | | |
|---|---|---|---|---|---|
| gtgagcgagc | acgtcaataa | gtacacggag | tacgaggcac | gtaccaaggc | gatcgaaacc | 60 |
| ttgctgtacg | agcgagggct | catcacgccc | gccgcggtcg | accgagtcgt | ttcgtactac | 120 |
| gagaacgaga | tcggcccgat | gggcggtgcc | aaggtcgtgg | ccaagtcctg | ggtggaccct | 180 |
| gagtaccgca | agtggctcga | agaggacgcg | acggccgcga | tggcgtcatt | gggctatgcc | 240 |
| ggtgagcagg | cacaccaaat | tcggcggtc | ttcaacgact | cccaaacgca | tcacgtggtg | 300 |
| gtgtgcactc | tgtgttcgtg | ctatccgtgg | ccggtgcttg | gtctcccgcc | cgcctggtac | 360 |
| aagagcatgg | agtaccggtc | ccgagtggta | gcggaccctc | gtggagtgct | caagcgcgat | 420 |
| ttcggtttcg | acatccccga | tgaggtggag | gtcagggttt | gggacagcag | ctccgaaatc | 480 |
| cgctacatcg | tcatcccgga | acggccggcc | ggcaccgacg | gttggtccga | ggaggagctg | 540 |
| acgaagctgg | tgagccggga | ctcgatgatc | ggtgtcagta | atgcgctcac | accgcaggaa | 600 |
| gtgatcgtat | ga | | | | | 612 |

<210> SEQ ID NO 2
<211> LENGTH: 203
<212> TYPE: PRT
<213> ORGANISM: Rhodococcus rhodochrous
<220> FEATURE:
<223> OTHER INFORMATION: alpha-subunit of nitrile hydratase of
      Rhodococcus rhodochrous

<400> SEQUENCE: 2

Val Ser Glu His Val Asn Lys Tyr Thr Glu Tyr Glu Ala Arg Thr Lys
1               5                   10                  15

Ala Ile Glu Thr Leu Leu Tyr Glu Arg Gly Leu Ile Thr Pro Ala Ala
            20                  25                  30

Val Asp Arg Val Val Ser Tyr Tyr Glu Asn Glu Ile Gly Pro Met Gly
        35                  40                  45

Gly Ala Lys Val Val Ala Lys Ser Trp Val Asp Pro Glu Tyr Arg Lys
    50                  55                  60

Trp Leu Glu Glu Asp Ala Thr Ala Ala Met Ala Ser Leu Gly Tyr Ala
65                  70                  75                  80

Gly Glu Gln Ala His Gln Ile Ser Ala Val Phe Asn Asp Ser Gln Thr
                85                  90                  95

His His Val Val Val Cys Thr Leu Cys Ser Cys Tyr Pro Trp Pro Val
            100                 105                 110

Leu Gly Leu Pro Pro Ala Trp Tyr Lys Ser Met Glu Tyr Arg Ser Arg
        115                 120                 125

Val Val Ala Asp Pro Arg Gly Val Leu Lys Arg Asp Phe Gly Phe Asp
    130                 135                 140

Ile Pro Asp Glu Val Glu Val Arg Val Trp Asp Ser Ser Ser Glu Ile
145                 150                 155                 160

Arg Tyr Ile Val Ile Pro Glu Arg Pro Ala Gly Thr Asp Gly Trp Ser
                165                 170                 175

Glu Glu Glu Leu Thr Lys Leu Val Ser Arg Asp Ser Met Ile Gly Val
            180                 185                 190

Ser Asn Ala Leu Thr Pro Gln Glu Val Ile Val
        195                 200

```
<210> SEQ ID NO 3
<211> LENGTH: 690
<212> TYPE: DNA
<213> ORGANISM: Rhodococcus rhodochrous
<220> FEATURE:
<223> OTHER INFORMATION: beta-subunit of nitrile hydratase of
      Rhodococcus rhodochrous

<400> SEQUENCE: 3
atggatggta tccacgacac aggcggcatg accggatacg gaccggtccc ctatcagaag      60
gacgagccct tcttccacta cgagtgggag ggtcggaccc tgtcaattct gacttggatg     120
catctcaagg gcatatcgtg gtgggacaag tcgcggttct ccgggagtc gatggggaac      180 gaaaactacg tcaacgagat cgcaactcg tactacaccc actggctgag tgcggcagaa      240
cgtatcctcg tcgccgacaa gatcatcacc gaagaagagc gaaagcaccg tgtgcaagag     300
atccttgagg gtcggtacac ggacaggaag ccgtcgcgga gttcgatcc ggcccagatc      360 gagaaggcga tcgaacggct tcacgagccc cactccctag cgcttccagg agcggagccg     420
agtttctctc tcggtgacaa gatcaaagtg aagagtatga accgctggg acacacacgg      480 tgcccgaaat atgtgcggaa caagatcggg gaaatcgtcg cctaccacgg ctgccagatc     540
tatcccgaga gcagctccgc cggcctcggc gacgatcctc gcccgctcta cacggtcgcg     600
ttttccgccc aggaactgtg gggcgacgac ggaaacggga agacgtagt gtgcgtcgat      660 ctctgggaac cgtacctgat ctctgcgtga                                      690

<210> SEQ ID NO 4
<211> LENGTH: 229
<212> TYPE: PRT
<213> ORGANISM: Rhodococcus rhodochrous
<220> FEATURE:
<223> OTHER INFORMATION: beta-subunit of nitrile hydratase of
      Rhodococcus rhodochrous

<400> SEQUENCE: 4

Met Asp Gly Ile His Asp Thr Gly Gly Met Thr Gly Tyr Gly Pro Val
1               5                   10                  15

Pro Tyr Gln Lys Asp Glu Pro Phe Phe His Tyr Glu Trp Glu Gly Arg
            20                  25                  30

Thr Leu Ser Ile Leu Thr Trp Met His Leu Lys Gly Ile Ser Trp Trp
        35                  40                  45

Asp Lys Ser Arg Phe Phe Arg Glu Ser Met Gly Asn Glu Asn Tyr Val
    50                  55                  60

Asn Glu Ile Arg Asn Ser Tyr Tyr Thr His Trp Leu Ser Ala Ala Glu
65                  70                  75                  80

Arg Ile Leu Val Ala Asp Lys Ile Ile Thr Glu Glu Glu Arg Lys His
                85                  90                  95

Arg Val Gln Glu Ile Leu Glu Gly Arg Tyr Thr Asp Arg Lys Pro Ser
            100                 105                 110

Arg Lys Phe Asp Pro Ala Gln Ile Glu Lys Ala Ile Glu Arg Leu His
        115                 120                 125

Glu Pro His Ser Leu Ala Leu Pro Gly Ala Glu Pro Ser Phe Ser Leu
    130                 135                 140

Gly Asp Lys Ile Lys Val Lys Ser Met Asn Pro Leu Gly His Thr Arg
145                 150                 155                 160

Cys Pro Lys Tyr Val Arg Asn Lys Ile Gly Glu Ile Val Ala Tyr His
                165                 170                 175

Gly Cys Gln Ile Tyr Pro Glu Ser Ser Ser Ala Gly Leu Gly Asp Asp
```

```
                180             185             190
Pro Arg Pro Leu Tyr Thr Val Ala Phe Ser Ala Gln Glu Leu Trp Gly
        195                 200                 205

Asp Asp Gly Asn Gly Lys Asp Val Val Cys Val Asp Leu Trp Glu Pro
        210                 215                 220

Tyr Leu Ile Ser Ala
225
```

METHOD FOR PREPARING AN AQUEOUS ACRYLAMIDE SOLUTION HAVING A LOW ACRYLIC ACID CONCENTRATION

The present invention relates to methods for preparing aqueous acrylamide solutions having a low acrylic acid concentration, aqueous acrylamide solutions obtainable by such methods, and acrylamide homopolymers or copolymers obtainable by polymerizing such acrylamide. In addition, the present invention is also directed to methods for reducing the acrylic acid concentration of aqueous acrylamide solutions.

Polyacrylamide is widely used as flocculants, as thickener in the paper industry, as additive in tertiary oil recovery, and many other fields. The raw material for polyacrylamide is typically its monomer acrylamide. In principal, there exist two different methods to produce acrylamide in industrial scales: Chemical synthesis and biological synthesis, wherein the biological synthesis methods are more and more on the rise due to milder reaction conditions and inherent process safety. Due to the milder reaction conditions, the absence of copper catalyst and the quantitative conversion of the nitrile, expensive downstream processing steps such as distillation or ion exchange can be avoided in the biological synthesis, thus resulting in cheaper plants with drastically reduced plant footprint.

Both synthesis methods use acrylonitrile as starting substance. While the chemical synthesis method uses copper catalysts (e.g., U.S. Pat. No. 4,048,226, U.S. Pat. No. 3,597,481), the biological synthesis method (also known as bio-based method) employs biocatalysts to hydrate (i.e. to convert) acrylonitrile in order to obtain acrylamide. Generally, such biocatalysts are microorganisms which are able to produce (i.e. which encode) the enzyme nitrile hydratase (IUBMB nomenclature as of Sep. 30, 2014: EC 4.2.1.84; CAS-No. 2391-37-5; also referred to as, e.g., NHase). Nitrile hydratase producing microorganisms are largely distributed in the environment and comprise, inter alia, representatives of the species *Rhodococcus rhodochrous, Rhodococcus pyridinovorans, Rhodococcus erythropolis, Rhodococcus equi, Rhodococcus ruber, Rhodococcus opacus, Aspergillus niger, Acidovorax avenae, Acidovorax facilis, Agrobacterium tumefaciens, Agrobacterium radiobacter, Bacillus subtilis, Bacillus pallidus, Bacillus smithii, Bacillus* sp BR449, *Bradyrhizobium oligotrophicum, Bradyrhizobium diazoefficiens, Bradyrhizobium japonicum, Burkholderia cenocepacia, Burkholderia gladioli, Klebsiella oxytoca, Klebsiella pneumonia, Klebsiella variicola, Mesorhizobium ciceri, Mesorhizobium opportunistum, Mesorhizobium* sp F28, *Moraxella, Pantoea endophytica, Pantoea agglomerans, Pseudomonas chlororaphis, Pseudomonas putida, Rhizobium, Rhodopseudomonas palustris, Serratia liquefaciens, Serratia marcescens, Amycolatopsis, Arthrobacter, Brevibacterium* sp CH1, *Brevibacterium* sp CH2, *Brevibacterium* sp R312, *Brevibacterium imperiale, Corynebacterium nitrilophilus, Corynebacterium pseudodiphteriticum, Corynebacterium glutamicum, Corynebacterium hoffmanii, Microbacterium imperiale, Microbacterium smegmatis, Micrococcus luteus, Nocardia globerula, Nocardia rhodochrous, Pseudonocardia thermophila, Trichoderma, Myrothecium verrucaria, Aureobasidium pullulans, Candida famata, Candida guilliermondii, Candida tropicalis, Cryptococcus flavus, Cryptococcus* sp UFMG-Y28, *Debaryomyces hanseii, Geotrichum candidum, Geotrichum* sp JR1, *Hanseniaspora, Kluyveromyces thermotolerans, Pichia kluyveri, Rhodotorula glutinis, Comomonas testosteroni, Pyrococcus abyssi, Pyrococcus furiosus,* and *Pyrococcus horikoshii.* (see, e.g., Prasad, Biotechnology Advances (2010), 28(6): 725-741; FR2835531). The enzyme nitrile hydratase is either iron- or cobalt-dependent (i.e. it possesses either an iron or a cobalt atom coordinated in its activity center) which is particularly characterized by its ability to catalyze conversion of acrylonitrile to obtain acrylamide by hydrating acrylonitrile (Kobayashi, Nature Biotechnology (1998), 16: 733-736).

The product of a biological synthesis method of converting acrylonitrile to acrylamide is a solution of acrylamide in water. However, in general the obtained aqueous acrylamide solution further contains acrylic acid, which is formed as a byproduct during the bioconversion.

Acrylamide is used as a monomer to form polymers of acrylamide. For the polymerization reactions, aqueous acrylamide solutions, which have been prepared by a biological synthesis method, can be used.

However, it has been found that acrylic acid, which is present in the aqueous acrylamide solutions used for the polymerization reactions, leads to reduced performance of the resulting acrylamide polymers. More specifically, the presence of acrylic acid can significantly impair the physical properties of the acrylamide polymer material, which e.g. leads to a reduced solubility and performance in various applications such as water treatment, paper making, oil recovery or mining.

Thus, there is a need for biocatalytic methods of preparing aqueous acrylamide solutions having a low concentration of acrylic acid.

This objective technical problem has been overcome by the present invention as defined in the claims and as described and exemplified herein below.

The present invention relates to a method for preparing an aqueous acrylamide solution, wherein the method comprises the following steps:
(a) adding the following components (i) to (iii) to a reactor to obtain a composition for bioconversion:
  (i) a biocatalyst capable of converting acrylonitrile to acrylamide;
  (ii) acrylonitrile;
  (iii) water; and
(b) performing a bioconversion on the composition obtained in step (a);
(c) adding further acrylonitrile and maintaining the content of acrylonitrile during step (b) at 0.3 w/w % or more for 10 minutes to 48 hours, preferably for 15 minutes to 24 hours, more preferably for 30 minutes to 18 hours and most preferably for 1 hour to 12 hours, wherein the indication of w/w % is referred to the total weight of the composition in the reactor.

In addition, the present invention is also related to a method for preparing an aqueous acrylamide solution, wherein the method comprises the following steps:
(a) adding the following components (i) to (iii) to a reactor to obtain a composition for bioconversion:
  (i) a biocatalyst capable of converting acrylonitrile to acrylamide;
  (ii) acrylonitrile;
  (iii) water; and
(b) performing a bioconversion on the composition obtained in step (a);
(c) adding further acrylonitrile and maintaining the content of acrylonitrile during step (b) at 0.3 w/w % or more until an acrylamide content of at least 20 w/w %, preferably of at least 25 w/w %, more preferably of at least 30 w/w %, even more preferably of at least 35 w/w %, still more preferably of at least 40 w/w %, still more preferably of at least 42.5 w/w %, still more preferably of at least 45 w/w %, still more preferably of at least 47.5 w/w % and most preferably of at least 50 w/w % is reached, wherein the indications of w/w % are each referred to the total weight of the composition in the reactor.

Also encompassed by the present invention is a method for reducing the acrylic acid concentration of an aqueous acrylamide solution, wherein the aqueous acrylamide solution is prepared by a process where acrylonitrile is converted to acrylamide using a biocatalyst and the method comprises the following steps:
(a) adding the following components (i) to (iii) to a reactor to obtain a composition for bioconversion:
  (i) a biocatalyst capable of converting acrylonitrile to acrylamide;
  (ii) acrylonitrile;
  (iii) water; and
(b) performing a bioconversion on the composition obtained in step (a);
(c) adding further acrylonitrile and maintaining the content of acrylonitrile during step (b) at 0.3 w/w % or more, wherein the indication of w/w % is referred to the total weight of the composition in the reactor.

Having regard to these methods for preparing an aqueous acrylamide solution, the inventors have found that by maintaining the content of acrylonitrile during the bioconversion in step (b) at 0.3 w/w % or more for 10 minutes to 48 hours, or by maintaining the content of acrylonitrile during the bioconversion in step (b) at 0.3 w/w % or more until an acrylamide content of at least 20 w/w % is reached, the concentration of acrylic acid in the obtained aqueous acrylamide solution is reduced. In addition, the inventors have found a method for reducing the acrylic acid concentration of an aqueous acrylamide solution, wherein by maintaining the content of acrylonitrile during step (b) at 0.3 w/w % or more the concentration of acrylic acid in the aqueous acrylamide solution is reduced. With reference to any one of the methods described herein for preparing an aqueous acrylamide solution or for reducing the acrylic acid concentration of an aqueous acrylamide solution, such a reduction of the acrylic acid concentration in the aqueous solution of acrylamide means that an aqueous acrylamide solution prepared according to any one of the methods of the present invention, wherein the content of acrylonitrile during the bioconversion in step (b) is maintained at 0.3 w/w % or more, has a lower concentration of acrylic acid compared to an aqueous acrylamide solution, which is prepared using a method, wherein the content of acrylonitrile during the bioconversion is not maintained at 0.3 w/w % or more.

The term "bioconversion" as used herein in the context with any one of the methods of the present invention in general denotes a reaction, wherein acrylonitrile is converted to acrylamide in the presence of water and a biocatalyst. The acrylamide is dissolved in the water, such that by any one of the methods described and provided herein an aqueous acrylamide solution is formed. As used herein, the term "composition" includes all components present in the reactor, such as, for example, the biocatalyst, acrylonitrile, acrylamide and water.

As used with regard to any one of the methods described herein, the term "biocatalyst" comprises in particular microorganisms (e.g., bacteria or protozoic eukaryotes) and enzymes which are capable of converting acrylonitrile to acrylamide. Methods for determining the ability of a given biocatalyst (e.g., microorganism or enzyme) to convert acrylonitrile to acrylamide are well known in the art. As an example, in context with any one of the methods of the present invention, activity of a given biocatalyst to be capable of converting acrylonitrile to acrylamide in the sense of the present invention may be determined as follows: First reacting 100 µl of a cell suspension, cell lysate, dissolved enzyme powder or any other preparation containing the supposed biocatalyst with 875 µl of an 50 mM potassium phosphate buffer and 25 µl of acrylonitrile at 25° C. on an eppendorf tube shaker at 1,000 rpm for 10 minutes. After 10 minutes of reaction time, samples may be drawn and immediately quenched by adding the same volume of 1.4% hydrochloric acid. After mixing of the sample, cells may be removed by centrifugation for 1 minute at 10,000 rpm and the amount of acrylamide formed is determined by analyzing the clear supernatant by HPLC. For affirmation of a biocatalyst to be capable of converting acrylonitrile to acrylamide in context with the present invention, the concentration of acrylamide shall be between 0.25 and 1.25 mmol/l—if necessary, the sample has to be diluted accordingly and the conversion has to be repeated. The activity may then be deduced from the concentration of acrylamide by dividing the acrylamide concentration derived from HPLC analysis by the reaction time, which has been 10 minutes and by multiplying this value with the dilution factor between HPLC sample and original sample. Activities>5 U/mg dry cell weight, preferably >25 U/mg dry cell weight, more preferably >50 U/mg dry cell weight, most preferably >100 U/mg dry cell weight indicate the presence of a functional biocatalyst and are considered as biocatalyst capable of converting acrylonitrile to acrylamide in context with the present invention.

More specifically, by employing any one of the methods of the present invention, the acrylic acid concentration of the composition at the end of the bioconversion may be 1500 ppm or less, preferably 1200 ppm or less, more preferably 1000 ppm or less, further preferably 750 ppm or less, even more preferably 500 ppm or less, still more preferably 300 ppm or less, still more preferably 200 ppm or less and most preferably 100 ppm or less, wherein indications of ppm each relate to weight parts and are each referred to the total weight of the composition at the end of the bioconversion. With this respect, the term "end of the bioconversion" denotes in any one of the methods described herein that a substantially full conversion of acrylonitrile to acrylamide has been reached. "Substantially full conversion of acrylonitrile to acrylamide" means, in particular, that the content of acrylonitrile of the composition is 1000 ppm or less, preferably 500 ppm or less, more preferably 200 ppm or less and most preferably 100 ppm or less, wherein indications of ppm each relate to weight parts and are each referred to the total weight of the composition. The acrylic acid concentration of the composition at the end of the bioconversion and/or the content of acrylonitrile may be determined using HPLC. Preferably, an HPLC method is used as set forth below under the Examples.

Accordingly, the present invention is also related to a method for preparing an aqueous acrylamide solution, wherein the method comprises the following steps:
(a) adding the following components (i) to (iii) to a reactor to obtain a composition for bioconversion:
  (i) a biocatalyst capable of converting acrylonitrile to acrylamide;
  (ii) acrylonitrile;
  (iii) water;
(b) performing a bioconversion on the composition obtained in step (a);
(c) adding further acrylonitrile and maintaining the content of acrylonitrile during step (b) at 0.3 w/w % or more, wherein the indication of w/w % is referred to the total weight of the composition in the reactor; and (d) obtaining a composition, wherein the acrylic acid concentration of the composition at the end of the bioconversion is 1500 ppm or less, preferably 1200 ppm or less, more preferably 1000 ppm or less, further preferably 750 ppm or less, even more preferably 500 ppm or less, still more preferably 300 ppm or less, still more preferably 200 ppm or less and most preferably 100 ppm or less, wherein indications of ppm each relate to weight parts and are each referred to the total weight of the composition at the end of the bioconversion.

In particular, the inventors have found that by carrying out any one of the methods of the present invention as described herein, the acrylic acid concentration may be reduced by at least 10%, preferably by at least 15%, more preferably by at least 20%, even more preferably by at least 25%, and most preferably by at least 35% compared to a reference method. In this context, the reduction of the acrylic acid concentration as defined in the methods of the present invention is related to the final concentration of acrylic acid contained in an aqueous acrylamide solution prepared by the method of the present invention (i.e. with maintaining the content of acrylonitrile during step (b) at 0.3 w/w % or more) compared to the final concentration of acrylic acid contained in an aqueous acrylamide solution not prepared by the methods of the present invention (i.e. without maintaining the content of acrylonitrile during step (b) at 0.3 w/w % or more as described herein).

In any one of the methods described and provided herein, acrylonitrile (component (ii)) is added to the reactor in step (a). In context with any one of the methods of the present invention, the acrylonitrile may be added to the reactor before the water is added, after water is added, or added together with water.

According to any one of the methods described herein, further acrylonitrile is added in step (c). With this respect, the acrylonitrile may be added continuously or intermittently. Addition of acrylonitrile may be at constant or variable feed rate or batch-wise. The acrylonitrile may be added in pure form or in solution. For example, an aqueous solution of acrylonitrile may be used.

In addition, in any one of the methods described and provided herein, water (component (iii)) is added to the reactor in step (a). The water may be added as such, be part of the biocatalyst as described herein, be part of an acrylonitrile solution as described herein, or otherwise be added. In case that the water is added as such, in general tap water or deionized water may be used. The water may also be part of an aqueous composition, such as an aqueous solution of a salt. In particular, a buffer may be employed.

For step (a) of any one of the methods described and provided herein, it is not relevant in which order components (i) to (iii) are added to the reactor.

Regarding the amounts of the components which are added, the biocatalyst, acrylonitrile and water may be added during steps (a) to (c) of any one of the methods described herein in a weight ratio of 0.001 to 0.5 w/w % of the biocatalyst, 22 to 45 w/w % of acrylonitrile and a balance to 100 w/w % of water; preferably of 0.005 to 0.2 w/w % of the biocatalyst, 26 to 42 w/w % of acrylonitrile and a balance to 100 w/w % of water; more preferably of 0.01 to 0.1 w/w % of the biocatalyst, 30 to 40 w/w % of acrylonitrile and a balance to 100 w/w % of water; most preferably of 0.015 to 0.065 w/w % of the biocatalyst, 35 to 39 w/w % of acrylonitrile and a balance to 100 w/w % of water, wherein in each case indications of w/w % are referred to the total weight (100 w/w %) of the combined weights of the biocatalyst, acrylonitrile and water added during steps (a) to (c). For example, in case of acrylonitrile, which is added in step (a) and step (c), this means that the combined amounts of acrylonitrile added in steps (a) and (c) are used for the calculation of the ratio. Indications of w/w % of the ratio of the biocatalyst may denote in each case the ratio of the biocatalyst in terms of the dry weight of the biocatalyst, in particular in terms of the dry cell weight of the biocatalyst. The water, which forms the balance to 100 w/w %, is not particularly limited. For example, the water may be an aqueous composition, such as an aqueous solution of a salt. In particular, a buffer may be used. However, it is preferred that the water is tap water or deionized water.

Step (b) of any one of the methods described and provided herein represents the bioconversion step during which acrylonitrile is converted to acrylamide by the biocatalyst as described and exemplified herein. More specifically, in any one of the methods described herein, the bioconversion in step (b) may be performed at 5° C. to 40° C. for 10 minutes to 48 hours, preferably at 5° C. to 35° C. for 10 minutes to 48 hours, more preferably at 15° C. to 30° C. for 10 minutes to 48 hours and most preferably at 20° C. to 28° C. for 10 minutes to 48 hours. In particular, such reaction temperatures are preferred from the viewpoint of high activity of the biocatalyst and reasonable reaction times. The actual time period to be applied for step (b) also depends on the desired acrylamide content of the aqueous acrylamide solution to be produced.

In addition to or independently of these temperature and time conditions, in any one of the methods of the present invention the content of acrylonitrile during step (b) may be maintained at 0.3 w/w % or more for 10 minutes to 48 hours, preferably for 15 minutes to 24 hours, more preferably for 30 minutes to 18 hours and most preferably for 1 hour to 12 hours. In particular, the content of acrylonitrile may be maintained at 0.3 w/w % or more for 2 hours to 12 hours, for 4 hours to 12 hours, for 6 hours to 12 hours, for 8 hours to 12 hours or for 10 hours to 12 hours during step (b).

According to any one of the methods described herein, the content of acrylonitrile may be maintained during step (b) at 0.3 w/w % or more until an acrylamide content of at least 20 w/w %, preferably of at least 25 w/w %, more preferably of at least 30 w/w %, even more preferably of at least 35 w/w %, still more preferably of at least 40 w/w %, still more preferably of at least 42.5 w/w %, still more preferably of at least 45 w/w %, still more preferably of at least 47.5 w/w % and most preferably of at least 50 w/w % is reached, wherein the indications of w/w % are each referred to the total weight of the composition in the reactor. After such a content of acrylamide is reached, the addition of acrylonitrile may be stopped. In any one of the methods described herein the acrylamide content of the composition in the reactor may be measured using Fourier Transform Infrared Spectroscopy (FTIR).

As set out above, in any one of the methods of the present invention, the content of acrylonitrile during the bioconversion of step (b) is maintained at 0.3 w/w % or more. Preferably, the content of acrylonitrile during step (b) is maintained at 0.4 w/w % or more, more preferably at 0.5 w/w % or more, even more preferably at 0.6 w/w % or more, still more preferably at 0.8 w/w % or more and most preferably at 1.0 w/w % or more, wherein the indications of w/w % are each referred to the total weight of the composition in the reactor. With this respect, the inventors have found that by increasing the content of acrylonitrile during step (b) the acrylic acid concentration can be further lowered.

In addition to maintaining a minimum value of the acrylonitrile content, in any one of the methods described herein the content of acrylonitrile is preferably maintained during step (b) at 6 w/w % or less, preferably at 5 w/w % or less, more preferably at 4 w/w % or less, most preferably at 3 w/w % or less, wherein the indications of w/w % are each referred to the total weight of the composition in the reactor. The inventors have found that maintaining the acrylonitrile content below such an upper limit allows for an excellent activity of the biocatalyst and for efficient reduction of the acrylic acid concentration in the obtained aqueous acrylamide solution. Moreover, a loss of activity of the biocatalyst may occur in case that the acrylonitrile content exceeds the value of 6 w/w %. In particular, the acrylonitrile content may be maintained during step (b) within a range of from 0.3 w/w % to 6 w/w %, preferably of from 0.4 w/w % to 5 w/w %, more preferably of from 0.5 w/w % to 4 w/w %, even more preferably of from 0.6 w/w % to 3 w/w %, still more preferably of from 0.8 w/w % to 3 w/w % most preferably of from 1.0 w/w % to 3 w/w %, wherein the indications of w/w % are each referred to the total weight of the composition in the reactor.

According to an embodiment of any one of the methods of the present invention, in particular of any one of the methods for preparing an aqueous acrylamide solution, the content of acrylonitrile is not 2 w/w % during the addition of the acrylonitrile, wherein the indication of w/w % is referred to the total weight of the composition in the reactor. This is in particular valid for the addition of acrylonitrile according to step (c).

As set out above, the activity of the biocatalyst may decrease in case that a high acrylonitrile content is maintained during the bioconversion of step (b). With this respect, the inventors have found that a loss of activity of the biocatalyst during the bioconversion is diminished if, after maintaining the acrylonitrile content in a first range during a first period of time, the acrylonitrile content is decreased to a second range and maintained in the second range during a second period of time. Accordingly, in order to achieve a high activity of the biocatalyst and thus reasonable reaction times, in any one of the methods described herein maintaining the acrylonitrile content at 0.3 w/w % or more during step (b) may comprise:
(i) maintaining an acrylonitrile content in a first range during a first period of time;
(ii) decreasing the acrylonitrile content to a second range; and
(iii) maintaining an acrylonitrile content in a second range during a second period of time.

In particular, by employing such a protocol, which comprises decreasing of the acrylonitrile content during the bioconversion, substantially full conversion of acrylonitrile to acrylamide can be achieved in the methods described herein.

Preferably, step (b) of any one of the methods of the present invention, wherein an acrylonitrile content is maintained in a first range during a first period of time, the acrylonitrile content is decreased to a second range, and the acrylonitrile content is maintained in a second range during a second period of time, comprises:
(i) maintaining an acrylonitrile content in a first range of from 1.2 w/w % to 6 w/w % during a first period of time of from 30 minutes to 4 hours;
(ii) decreasing the acrylonitrile content to a second range; and
(iii) maintaining an acrylonitrile content in a second range of from 0.3 w/w % to 1.2 w/w % during a second period of time of from 30 minutes to 24 hours,
wherein the indications of w/w % are each referred to the total weight of the composition in the reactor.

More preferably, step (b) of any one of the methods described herein comprises:
(i) maintaining an acrylonitrile content in a first range of from 1.2 w/w % to 4 w/w % during a first period of time of from 30 minutes to 3 hours;
(ii) decreasing the acrylonitrile content to a second range; and
(iii) maintaining an acrylonitrile content in a second range of from 0.5 w/w % to 1.1 w/w % during a second period of time of from 30 minutes to 12 hours,
wherein the indications of w/w % are each referred to the total weight of the composition in the reactor.

Most preferably, step (b) of any one of the methods of the present invention comprises:
(i) maintaining an acrylonitrile content in a first range of from 1.3 w/w % to 3 w/w % during a first period of time of from 30 minutes to 2 hours;
(ii) decreasing the acrylonitrile content to a second range; and
(iii) maintaining an acrylonitrile content in a second range of from 0.6 w/w % to 1.0 w/w % during a second period of time of from 1 hour to 8 hours, preferably of from 1 hour to 5 hours, wherein the indications of w/w % are each referred to the total weight of the composition in the reactor.

Any one of the methods described herein may be carried out using a continuous process. In particular, the term "continuous process" as used herein refers to a method, wherein an aqueous acrylamide solution is produced in a continuous manner without collecting the entire reaction mixture in the reactor. This means that the raw materials for the reaction, which may comprise the biocatalyst, water and acrylonitrile, are fed to the reactor continuously or intermittently and that the obtained product is recovered from the reactor continuously or intermittently.

Alternatively, any one of the methods of the present invention may be carried out using a semi-batch process. In particular, the term "semi-batch process" as used herein may comprise that an aqueous acrylamide solution is produced in a discontinuous manner. According to a non-limiting example for carrying out such a semi-batch process water, a certain amount of acrylonitrile and the biocatalyst are placed in a reactor. Further acrylonitrile is then added during the bioconversion until a desired content of acrylamide of the composition is reached. After such desired content of acrylamide is reached, the obtained composition is entirely recovered from the reactor, before new reactants are placed therein.

Regarding the feeding of acrylonitrile during the bioconversion step (b), according to a non-limiting embodiment of any one of the methods of the present invention the acrylonitrile may be fed such that the content of acrylonitrile during step (b) is maintained within a range of ±10 w/w %, preferably of ±5 w/w %, more preferably of ±2 w/w %, most preferably of ±1 w/w % of a predetermined value of the acrylonitrile content, wherein the indications of w/w % are each referred to the total weight of acrylonitrile in the reactor. In particular, in any one of the methods of the present invention the acrylonitrile may be fed such that the content of acrylonitrile during step (b) is maintained substantially constant at a predetermined value.

In general, in any one of the methods of the present invention the acrylonitrile content and/or the acrylamide content during step (b) may be measured using Fourier Transform Infrared Spectroscopy (FTIR). In particular, the acrylonitrile content and/or the acrylamide content may be measured online using FTIR.

In accordance with any one of the methods of the present invention, the biocatalyst capable of converting acrylonitrile to acrylamide may be a microorganism which encodes the enzyme nitrile hydratase. With this regard, it is not relevant for the present invention whether the microorganism is naturally encoding nitrile hydratase, or whether it has been genetically modified to encode said enzyme, or whether a microorganism naturally encoding nitrile hydratase has been modified such as to be able to produce more and/or enhanced nitrile hydratase. As used herein, the expression "biocatalyst (e.g., microorganism) encoding (the enzyme) nitrile hydratase" or the like generally means that such a microorganism is generally also able to produce and stably maintain nitrile hydratase. That is, as used herein and as readily understood by the skilled person, a biocatalyst (e.g., a microorganism) to be employed in accordance with the present invention which (naturally or non-naturally) encodes nitrile hydratase is generally also capable of producing and stably maintaining nitrile hydratase. However, in accordance with the present invention, it is also possible that such microorganisms only produced nitrile hydratase during cultivation (or fermentation) of the microorganism—thus then containing nitrile hydratase—before being added to a reactor according to step (a) of any one of the methods described and provided herein. In such a case, it is possible that the microorganisms do not produce nitrile hydratase during the methods described and provided herein any more, but they act only via the nitrile hydratase units which they have produced before and which they still contain. As readily understood by the person skilled in the art, it is also possible that some nitrile hydratase molecules may leave the microorganism (e.g., due to lysis of the microorganism) and act freely in the solution as biocatalyst. As such, it also possible that the term "biocatalyst" as used herein encompasses the enzyme nitrile hydratase per se, as long as it is able to convert acrylonitrile to acrylamide as described and exemplified herein. In context with the present invention, it is also possible to directly employ nitrile hydratase as biocatalyst.

In context with the present invention, microorganisms naturally encoding nitrile hydratase, which can be used as biocatalyst in any one of the methods described herein, comprise species belonging to a genus selected from the group consisting of *Rhodococcus, Aspergillus, Acidovorax, Agrobacterium, Bacillus, Bradyrhizobium, Burkholderia, Escherichia, Geobacillus, Klebsiella, Mesorhizobium, Moraxella, Pantoea, Pseudomonas, Rhizobium, Rhodopseudomonas, Serratia, Amycolatopsis, Arthrobacter, Brevibacterium, Corynebacterium, Microbacterium, Micrococcus, Nocardia, Pseudonocardia, Trichoderma, Myrothecium, Aureobasidium, Candida, Cryptococcus, Debaryomyces, Geotrichum, Hanseniaspora, Kluyveromyces, Pichia, Rhodotorula, Comomonas*, and *Pyrococcus*. In preferred embodiments of the invention the biocatalyst is selected from bacteria of the genus *Rhodococcus, Pseudomonas, Escherichia* and *Geobacillus*.

Preferred biocatalysts to be employed in context with any one of the methods of the present invention comprise representatives of the genus *Rhodococcus*. Species suitable as biocatalyst to be employed in context with any one of the methods of the present invention may comprise, e.g., *Rhodococcus rhodochrous* (e.g., NCIMB 41164, J1/FERM-BP 1478, M33 or M8), *Rhodococcus pyridinovorans, Rhodococcus erythropolis, Rhodococcus equi, Rhodococcus ruber, Rhodococcus opacus, Aspergillus niger, Acidovorax avenae, Acidovorax facilis, Agrobacterium tumefaciens, Agrobacterium radiobacter, Bacillus subtilis, Bacillus pallidus, Bacillus smithii, Bacillus* sp BR449, *Bradyrhizobium oligotrophicum, Bradyrhizobium diazoefficiens, Bradyrhizobium japonicum, Burkholderia cenocepacia, Burkholderia gladioli, Escherichia coli, Geobacillus* sp. RAPc8, *Klebsiella oxytoca, Klebsiella pneumonia, Klebsiella variicola, Mesorhizobium ciceri, Mesorhizobium opportunistum, Mesorhizobium* sp F28, *Moraxella, Pantoea endophytica, Pantoea agglomerans, Pseudomonas chlororaphis, Pseudomonas putida, Rhizobium, Rhodopseudomonas palustris, Serratia liquefaciens, Serratia marcescens, Amycolatopsis, Arthrobacter, Brevibacterium* sp CH1, *Brevibacterium* sp CH2, *Brevibacterium* sp R312, *Brevibacterium imperiale, Brevibacterium casei, Corynebacterium nitrilophilus, Corynebacterium pseudodiphteriticum, Corynebacterium glutamicum, Corynebacterium hoffmanii, Microbacterium imperiale, Microbacterium smegmatis, Micrococcus luteus, Nocardia globerula, Nocardia rhodochrous, Nocardia* sp 163, *Pseudonocardia thermophila, Trichoderma, Myrothecium verrucaria, Aureobasidium pullulans, Candida famata, Candida guilliermondii, Candida tropicalis, Cryptococcus flavus, Cryptococcus* sp UFMG-Y28, *Debaryomyces hanseii, Geotrichum candidum, Geotrichum* sp JR1, *Hanseniaspora, Kluyveromyces thermotolerans, Pichia kluyveri, Rhodotorula glutinis, Comomonas testosteroni, Pyrococcus abyssi, Pyrococcus furiosus*, or *Pyrococcus horikoshii*.

According to one embodiment of any one of the methods of the present invention, the biocatalyst to be employed belongs to the species *Rhodococcus rhodochrous*. Particular examples for strains belonging to *Rhodococcus rhodochrous* which may be employed in context with any one of the methods described herein comprise NCIMB 41164, J1 (FERM-BP 1478), M33 and M8.

Alternatively or in addition to *Rhodococcus rhodochrous*, the biocatalyst employed in any one of the methods described herein may be *Rhodococcus pyridinovorans*.

In context with the present invention, nitrile hydratase encoding microorganisms which are not naturally encoding nitrile hydratase may be genetically engineered microorganisms which naturally do not contain a gene encoding a nitrile hydratase but which have been manipulated such as to contain a polynucleotide encoding a nitrile hydratase (e.g., via transformation, transduction, transfection, conjugation, or other methods suitable to transfer or insert a polynucleotide into a cell as known in the art; cf. Sambrook and Russell 2001, Molecular Cloning: A Laboratory Manual, CSH Press, Cold Spring Harbor, N.Y., USA), thus enabling the microorganisms to produce and stably maintain the nitrile hydratase enzyme. For this purpose, it may further be required to insert additional polynucleotides which may be necessary to allow transcription and translation of the nitrile hydratase gene or mRNA, respectively. Such additional polynucleotides may comprise, inter alia, promoter sequences, polyT- or polyU-tails, or replication origins or other plasmid-control sequences. In this context, such genetically engineered microorganisms which naturally do not contain a gene encoding a nitrile hydratase but which have been manipulated such as to contain a polynucleotides encoding a nitrile hydratase may be prokaryotic or eukaryotic microorganisms. Examples for such prokaryotic microorganisms include, e.g., representatives of the species

*Escherichia coli.* Examples for such eukaryotic microorganisms include, e.g., yeast (e.g., *Saccharomyces cerevisiae*).

In context of the present invention, the term "nitrile hydratase" (also referred to herein as NHase) generally means an enzyme which is capable of catalyzing the conversion (i.e. hydration) of acrylonitrile to acrylamide. Such an enzyme may be, e.g., the enzyme registered under IUBMB nomenclature as of Sep. 30, 2014: EC 4.2.1.84; CAS-No. 2391-37-5. However, the term "nitrile hydratase" as used herein also encompasses modified or enhanced enzymes which are, e.g., capable of converting acrylonitrile to acrylamide more quickly, or which can be produced at a higher yield/time-ratio, or which are more stable, as long as they are capable to catalyze conversion (i.e. hydration) of acrylonitrile to acrylamide. Methods for determining the ability of a given biocatalyst (e.g., microorganism or enzyme) for catalyzing the conversion of acrylonitrile to acrylamide are known in the art. As an example, in context with the present invention, activity of a given biocatalyst to act as a nitrile hydratase in the sense of the present invention may be determined as follows: First reacting 100 μl of a cell suspension, cell lysate, dissolved enzyme powder or any other preparation containing the supposed nitrile hydratase with 875 μl of an 50 mM potassium phosphate buffer and 25 μl of acrylonitrile at 25° C. on an eppendorf tube shaker at 1,000 rpm for 10 minutes. After 10 minutes of reaction time, samples may be drawn and immediately quenched by adding the same volume of 1.4% hydrochloric acid. After mixing of the sample, cells may be removed by centrifugation for 1 minute at 10,000 rpm and the amount of acrylamide formed is determined by analyzing the clear supernatant by HPLC. For affirmation of an enzyme to be a nitrile hydratase in context with the present invention, the concentration of acrylamide shall be between 0.25 and 1.25 mmol/l—if necessary, the sample has to be diluted accordingly and the conversion has to be repeated. The enzyme activity may then be deduced from the concentration of acrylamide by dividing the acrylamide concentration derived from HPLC analysis by the reaction time, which has been 10 minutes and by multiplying this value with the dilution factor between HPLC sample and original sample. Activities >5 U/mg dry cell weight, preferably >25 U/mg dry cell weight, more preferably >50 U/mg dry cell weight, most preferably >100 U/mg dry cell weight indicate the presence of a functionally expressed nitrile hydratase and are considered as nitrile hydratase in context with the present invention.

In context with the present invention, the nitrile hydratase may be a polypeptide encoded by a polynucleotide which comprises or consists of a nucleotide sequence which is at least 70%, preferably at least 75%, more preferably at least 80%, more preferably at least 85%, more preferably at least 90%, more preferably at least 95%, more preferably at least 96%, more preferably at least 97%, more preferably at least 98%, more preferably at least 99%, more preferably at least 99.5%, and most preferably 100% identical to the nucleotide sequence of SEQ ID NO: 1 (alpha-subunit of nitrile hydratase of *R. rhodochrous*:

GTGAGCGAGCACGTCAATAAGTACACGGAGTACGAGGCACGTACCAA

GGCGATCGAAACCTTGCTGTACGAGCGAGGGCTCATCACGCCCGCCG

CGGTCGACCGAGTCGTTTCGTACTACGAGAACGAGATCGGCCCGATG

GGCGGTGCCAAGGTCGTGGCCAAGTCCTGGGTGGACCCTGAGTACCG

CAAGTGGCTCGAAGAGGACGCGACGGCCGCGATGGCGTCATTGGGCT

ATGCCGGTGAGCAGGCACACCAAATTTCGGCGGTCTTCAACGACTCC

CAAACGCATCACGTGGTGGTGTGCACTCTGTGTTCGTGCTATCCGTG

GCCGGTGCTTGGTCTCCCGCCCGCCTGGTACAAGAGCATGGAGTACC

GGTCCCGAGTGGTAGCGGACCCTCGTGGAGTGCTCAAGCGCGATTTC

GGTTTCGACATCCCCGATGAGGTGGAGGTCAGGGTTTGGGACAGCAG

CTCCGAAATCCGCTACATCGTCATCCCGGAACGGCCGGCCGGCACCG

ACGGTTGGTCCGAGGAGGAGCTGACGAAGCTGGTGAGCCGGGACTCG

ATGATCGGTGTCAGTAATGCGCTCACACCGCAGGAAGTGATCGTATG

A)

and/or to the nucleotide sequence of SEQ ID NO: 3 (beta-subunit of nitrile hydratase of *R. rhodochrous*:

ATGGATGGTATCCACGACACAGGCGGCATGACCGGATACGGACCGGT

CCCCTATCAGAAGGACGAGCCCTTCTTCCACTACGAGTGGGAGGGTC

GGACCCTGTCAATTCTGACTTGGATGCATCTCAAGGGCATATCGTGG

TGGGACAAGTCGCGGTTCTTCCGGGAGTCGATGGGGAACGAAAACTA

CGTCAACGAGATTCGCAACTCGTACTACACCCACTGGCTGAGTGCGG

CAGAACGTATCCTCGTCGCCGACAAGATCATCACCGAAGAAGAGCGA

AAGCACCGTGTGCAAGAGATCCTTGAGGGTCGGTACACGGACAGGAA

GCCGTCGCGGAAGTTCGATCCGGCCCAGATCGAGAAGGCGATCGAAC

GGCTTCACGAGCCCCACTCCCTAGCGCTTCCAGGAGCGGAGCCGAGT

TTCTCTCTCGGTGACAAGATCAAAGTGAAGAGTATGAACCCGCTGGG

ACACACACGGTGCCCGAAATATGTGCGGAACAAGATCGGGGAAATCG

TCGCCTACCACGGCTGCCAGATCTATCCCGAGAGCAGCTCCGCCGGC

CTCGGCGACGATCCTCGCCCGCTCTACACGGTCGCGTTTTCCGCCCA

GGAACTGTGGGCGACGACGGAAACGGGAAAGACGTAGTGTGCGTCG

ATCTCTGGGAACCGTACCTGATCTCTGCGTGA), provided that the polypeptide encoded by said polynucleotide is capable of catalyzing hydration of acrylonitrile to acrylamide (i.e. has nitrile hydratase activity) as described and exemplified herein. Also in the context with the present invention, the nitrile hydratase may be a polypeptide which comprises or consists of an amino acid sequence which is at least 70%, preferably at least 75%, more preferably at least 80%, more preferably at least 85%, more preferably at least 90%, more preferably at least 95%, more preferably at least 96%, more preferably at least 97%, more preferably at least 98%, more preferably at least 99%, more preferably at least 99.5%, and most preferably 100% identical to the amino acid sequence of SEQ ID NO: 2 (alpha-subunit of nitrile hydratase of *R. rhodochrous*:

VSEHVNKYTE YEARTKAIET LLYERGLITP AAVDRVVSYY

ENEIGPMGGA KVVAKSWVDP EYRKWLEEDA TAAMASLGYA

GEQAHQISAV FNDSQTHHVV VCTLCSCYPW PVLGLPPAWY

```
KSMEYRSRVV ADPRGVLKRD FGFDIPDEVE VRVWDSSSEI

RYIVIPERPA GTDGWSEEEL TKLVSRDSMI GVSNALTPQE

VIV)
``` and/or to the amino acid sequence of SEQ ID NO: 4 (beta-subunit of nitrile hydratase of R. rhodochrous:

```
MDGIHDTGGM TGYGPVPYQK DEPFFHYEWE GRTLSILTWM

HLKGISWWDK SRFFRESMGN ENYVNEIRNSY YTHWLSAAE

RILVADKIIT EEERKHRVQE ILEGRYTDRK PSRKFDPAQI

EKAIERLHEP HSLALPGAEP SFSLGDKIKV KSMNPLGHTR

CPKYVRNKIG EIVAYHGCQI YPESSSAGLG DDPRPLYTVA

FSAQELWGDD GNGKDVVCVD LWEPYLISA).
``` provided that said polypeptide is capable of catalyzing hydration of acrylonitrile to acrylamide as described and exemplified herein.

The level of identity between two or more sequences (e.g., nucleic acid sequences or amino acid sequences) can be easily determined by methods known in the art, e.g., by BLAST analysis. Generally, in context with the present invention, if two sequences (e.g., polynucleotide sequences or amino acid sequences) to be compared by, e.g., sequence comparisons differ in identity, then the term "identity" may refer to the shorter sequence and that part of the longer sequence that matches said shorter sequence. Therefore, when the sequences which are compared do not have the same length, the degree of identity may preferably either refer to the percentage of nucleotide residues in the shorter sequence which are identical to nucleotide residues in the longer sequence or to the percentage of nucleotides in the longer sequence which are identical to nucleotide sequence in the shorter sequence. In this context, the skilled person is readily in the position to determine that part of a longer sequence that matches the shorter sequence. Furthermore, as used herein, identity levels of nucleic acid sequences or amino acid sequences may refer to the entire length of the respective sequence and is preferably assessed pair-wise, wherein each gap is to be counted as one mismatch. These definitions for sequence comparisons (e.g., establishment of "identity" values) are to be applied for all sequences described and disclosed herein.

Moreover, the term "identity" as used herein means that there is a functional and/or structural equivalence between the corresponding sequences. Nucleic acid/amino acid sequences having the given identity levels to the herein-described particular nucleic acid/amino acid sequences may represent derivatives/variants of these sequences which, preferably, have the same biological function. They may be either naturally occurring variations, for instance sequences from other varieties, species, etc., or mutations, and said mutations may have formed naturally or may have been produced by deliberate mutagenesis. Furthermore, the variations may be synthetically produced sequences. The variants may be naturally occurring variants or synthetically produced variants or variants produced by recombinant DNA techniques. Deviations from the above-described nucleic acid sequences may have been produced, e.g., by deletion, substitution, addition, insertion and/or recombination. The term "addition" refers to adding at least one nucleic acid residue/amino acid to the end of the given sequence, whereas "insertion" refers to inserting at least one nucleic acid residue/amino acid within a given sequence. The term "deletion" refers to deleting or removal of at least one nucleic acid residue or amino acid residue in a given sequence. The term "substitution" refers to the replacement of at least one nucleic acid residue/amino acid residue in a given sequence. Again, these definitions as used here apply, mutatis mutandis, for all sequences provided and described herein.

Generally, as used herein, the terms "polynucleotide" and "nucleic acid" or "nucleic acid molecule" are to be construed synonymously. Generally, nucleic acid molecules may comprise inter alia DNA molecules, RNA molecules, oligonucleotide thiophosphates, substituted ribo-oligonucleotides or PNA molecules. Furthermore, the term "nucleic acid molecule" may refer to DNA or RNA or hybrids thereof or any modification thereof that is known in the art (see, e.g., U.S. Pat. No. 5,525,711, U.S. Pat. No. 4,711,955, U.S. Pat. No. 5,792,608 or EP 302175 for examples of modifications). The polynucleotide sequence may be single- or double-stranded, linear or circular, natural or synthetic, and without any size limitation. For instance, the polynucleotide sequence may be genomic DNA, cDNA, mitochondrial DNA, mRNA, antisense RNA, ribozymal RNA or a DNA encoding such RNAs or chimeroplasts (Gamper, Nucleic Acids Research, 2000, 28, 4332-4339). Said polynucleotide sequence may be in the form of a vector, plasmid or of viral DNA or RNA. Also described herein are nucleic acid molecules which are complementary to the nucleic acid molecules described above and nucleic acid molecules which are able to hybridize to nucleic acid molecules described herein. A nucleic acid molecule described herein may also be a fragment of the nucleic acid molecules in context of the present invention. Particularly, such a fragment is a functional fragment. Examples for such functional fragments are nucleic acid molecules which can serve as primers.

When adding the biocatalyst to the reactor in any one of the methods of the present invention, the biocatalyst may be taken directly from the fermentation broth. It is further envisaged that the biocatalyst may be employed in the form of a fermentation broth in the methods disclosed herein. Thus, the biocatalyst does not need to be isolated from the fermentation broth, and a fermentation broth comprising the biocatalyst may be used for the bioconversion. For example, a fermentation broth comprising the biocatalyst may be added to the reactor in step (a) of the methods of the present invention. Alternatively, in accordance with any one of the methods described herein, the biocatalyst may have been dried before being added to the reactor. In this context the term "before" does not necessarily mean that the biocatalyst has been dried and is then directly added to the reactor. It is rather sufficient that the biocatalyst has undergone a drying step at any time before it is added to the reactor, independently of whether further steps between the drying and the addition are performed or not. As non-limiting examples, such further steps between the drying step and the addition to the reactor may be storage or reconstitution. However, it is also possible to add the biocatalyst to the reactor directly after drying. The inventors have surprisingly found that by using a biocatalyst, which has undergone a drying step, the concentration of acrylic acid in an aqueous acrylamide solution obtained by any one of the methods described herein is further reduced in comparison to the case that a biocatalyst is used which has not undergone drying before being employed in the bioconversion.

Regarding the drying method, in any one of the methods described an provided herein, a biocatalyst may be used which has been dried using freeze-drying, spray drying, heat drying, vacuum drying, fluidized bed drying and/or spray granulation. With this respect, spray drying and freeze drying are preferred, since in general by using a biocatalyst, which has been subjected to spray- or freeze drying, a higher reduction of the acrylic acid concentration in the obtained aqueous acrylamide solutions is achieved compared to employing a biocatalyst which has been dried using other methods.

According to any one of the methods of the present invention a dried biocatalyst may be added to the reactor. This means that the biocatalyst is added to the reactor in a dried form. In particular, the biocatalyst may have the form of a powder or a granule. As an alternative to adding a dried biocatalyst to the reactor, the dried biocatalyst may be reconstituted before being added to the reactor. For example, the biocatalyst may be reconstituted by suspending in an aqueous composition. With this respect, the aqueous composition may be water or a buffer. As a further alternative, a biocatalyst in form of a matrix bound microorganism may be added to the reactor.

The term "dried biocatalyst" as used herein refers to a biocatalyst that has been subjected to a drying step. A dried biocatalyst typically has a moisture content of less than about 20 w/w %, more preferably less than about 15 w/w %, even more preferably less than about 14 w/w %, most preferably from about 5 to about 10 w/w % based on the total weight of the biocatalyst sample. Methods of determining the moisture content are familiar to the skilled person. For example, in the context of the present invention the moisture content of a sample of the dried biocatalyst may be determined via thermogravimetric analysis. At the beginning of the thermogravimetric analysis the initial weight of the sample is determined. The sample is then heated and the moisture vaporizes. Heating is continued until the sample weight remains constant. The difference between the constant weight at the end of the analysis and the initial weight represents the amount of water vaporized during the analysis, which allows for calculation of the moisture content of the sample. For determination of the moisture content via thermogravimetric analysis, the biocatalyst sample may be, for example, analyzed on a 'Mettler Toledo HB43-S Halogen moisture analyzer', operated at 130° C. until the sample weight remains constant for at least 30 seconds.

By performing any one of the methods described herein the aqueous acrylamide solution may be obtained along with the biocatalyst. Accordingly, the biocatalyst may be separated from the obtained aqueous acrylamide solution. Such a separation of the biocatalyst may be performed with regard to the desired applications, which may, for example, include the homopolymerization or copolymerization of the acrylamide. Suitable methods for separation of the biocatalyst are known in the art and include, for example, centrifugation, sedimentation (e.g., with flocculation), membrane separation and filtration.

The present invention further relates to aqueous acrylamide solutions obtainable or being obtained by any one of the methods described and provided herein.

An aqueous acrylamide solution, in particular an aqueous acrylamide solution obtainable or being obtained by any one of the methods described herein, may contain 35 to 65 w/w % of acrylamide and may have an acrylic acid concentration of not more than 1500 ppm, preferably of not more than 1000 ppm, more preferably of not more than 750 ppm, further preferably of not more than 500 ppm, even more preferably of not more than 300 ppm, still more preferably of not more than 200 ppm and most preferably of not more than 100 ppm, wherein indications of w/w % and ppm are each referred to the total weight of the solution, and ppm each relates to weight parts.

Preferably, the aqueous acrylamide solution contains 40 to 60 w/w % of acrylamide and has an acrylic acid concentration of not more than 1500 ppm, preferably of not more than 1000 ppm, more preferably of not more than 750 ppm, further preferably of not more than 500 ppm, even more preferably of not more than 300 ppm, still more preferably of not more than 200 ppm and most preferably of not more than 100 ppm, wherein indications of w/w % and ppm are each referred to the total weight of the solution, and ppm each relates to weight parts.

More preferably, the aqueous acrylamide contains 45 to 55 w/w % of acrylamide and has an acrylic acid concentration of not more than 1500 ppm, preferably of not more than 1000 ppm, more preferably of not more than 750 ppm, further preferably of not more than 500 ppm, even more preferably of not more than 300 ppm, still more preferably of not more than 200 ppm and most preferably of not more than 100 ppm, wherein indications of w/w % and ppm are each referred to the total weight of the solution and ppm each relates to weight parts.

Most preferably, the aqueous acrylamide solution contains 50 to 54 w/w % of acrylamide and has an acrylic acid concentration of not more than 1500 ppm, preferably of not more than 1000 ppm, more preferably of not more than 750 ppm, further preferably of not more than 500 ppm, even more preferably of not more than 300 ppm, still more preferably of not more than 200 ppm and most preferably of not more than 100 ppm, wherein indications of w/w % and ppm are each referred to the total weight of the solution and ppm each relates to weight parts.

In any one of the aqueous acrylamide solutions, the acrylamide content and/or the acrylic acid concentration may be determined using HPLC. Preferably, an HPLC method is used as set forth below under the Examples.

Furthermore, the present invention relates to an acrylamide homopolymer or copolymer obtainable or being obtained by polymerizing the acrylamide of the aqueous solution as described herein. With this respect, in case of a homopolymer the term "polymerizing" refers to a homopolymerization reaction, while in case of a copolymer the term "polymerizing" refers to a copolymerization reaction. The homopolymerization or copolymerization may be performed using an aqueous acrylamide solution obtainable or being obtained by any one of the methods described herein. In particular, an aqueous acrylamide solution may be used, from which the biocatalyst has been separated prior to the polymerization. Alternatively, the acrylamide may have been isolated from the aqueous acrylamide solution before being subjected to homopolymerization or copolymerization.

An acrylamide homopolymer or copolymer, in particular an acrylamide homopolymer or copolymer obtainable or being obtained by polymerizing the acrylamide of the aqueous solution as described herein, may have an acrylic acid content of 60,000 ppm or less, preferably of 20,000 ppm or less, more preferably of 10,000 ppm or less, and most preferably of 2,000 ppm or less, wherein the indications of ppm each relate to weight parts and are each referred to the total weight of the solid acrylamide homopolymer or copolymer.

High acrylic acid contents within acrylamide solutions can lead to reduced performance of the resulting polyacrylamide homopolymers and copolymers, especially for cationic polyacrylamide products, i.e. copolymers of acrylamide with cationic co-monomers. This is highly evident for cationic copolymers with low cationic co-monomer contents. Without wishing to be bound by any theory, molar equivalent amounts of anionic acrylic acid and the cationic co-monomers within the copolymer chain results in the generation of charge complexes. This can significantly impair the physical properties of the polyacrylamide material, reducing solubility and performance in applications such as water treatment, paper making, oil recovery or mining.

Regarding this impact of acrylic acid, the acrylamide homopolymer or copolymer described and provided herein is preferably a cationic polyacrylamide. As generally known to a person skilled in the art, the term "cationic polyacrylamide" denotes a copolymer which in addition to acrylamide monomers contains cationic co-monomers, such as, e.g., co-monomers which comprise quaternary ammonium groups. Particularly preferred is a cationic polyacrylamide having an acrylic acid content of 60,000 ppm or less, preferably of 20,000 ppm or less, more preferably of 10,000 ppm or less, and most preferably of 2,000 ppm or less, wherein the indications of ppm each relate to weight parts and are each referred to the total weight of the solid acrylamide homopolymer or copolymer.

In general, the acrylic acid content of any polymer or copolymer described herein may be determined using methods known in the art, e.g., NMR spectroscopy as described in European Polymer Journal (2007), 43(3): 824-834.

Acrylamide homopolymers and/or copolymers are, for example, used in oilfield applications. In particular, use of acrylamide homopolymers and/or copolymers is made in tertiary oil recovery, which is also denoted as enhanced oil recovery. With this respect, in methods of tertiary oil recovery an aqueous solution of the polymer may be injected into the rock in order to promote oil displacement and thus increase the yield of crude oil. The present invention is therefore also related to an aqueous solution of any acrylamide homopolymer and/or copolymer described herein. As the water for the aqueous solution seawater may be used.

This description includes information that may be useful in understanding the present invention. It is not an admission that any of the information provided herein is prior art or relevant to the presently claimed inventions, or that any publication specifically or implicitly referenced is prior art.

It is to be noted that as used herein, the singular forms "a", "an", and "the", include plural references unless the context clearly indicates otherwise. Thus, for example, reference to "a reagent" includes one or more of such different reagents and reference to "the method" includes reference to equivalent steps and methods known to those of ordinary skill in the art that could be modified or substituted for the methods described herein.

Those skilled in the art will recognize, or be able to ascertain, using not more than routine experimentation, many equivalents to the specific embodiments of the invention described herein. Such equivalents are intended to be encompassed by the present invention.

Unless otherwise indicated, the term "at least" preceding a series of elements is to be understood to refer to every element in the series. Those skilled in the art will recognize, or be able to ascertain using no more than routine experimentation, many equivalents to the specific embodiments of the methods and uses described herein. Such equivalents are intended to be encompassed by the present invention.

Several documents are cited throughout the text of this disclosure. Each of the documents cited herein (including all patents, patent applications, scientific publications, manufacturer's specifications, instructions, etc.), whether supra or infra, are hereby incorporated by reference in their entirety. To the extent the material incorporated by reference contradicts or is inconsistent with this specification, the specification will supersede any such material. Nothing herein is to be construed as an admission that the invention is not entitled to antedate such disclosure by virtue of prior invention.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integer or step. When used herein the term "comprising" can be substituted with the term "containing" or sometimes when used herein with the term "having".

When used herein "consisting of" excludes any element, step, or ingredient not specified in the claim element. When used herein, "consisting essentially of" does not exclude materials or steps that do not materially affect the basic and novel characteristics of the claim. In each instance herein any of the terms "comprising", "consisting essentially of" and "consisting of" may be replaced with either of the other two terms.

As used herein, the conjunctive term "and/or" between multiple recited elements is understood as encompassing both individual and combined options. For instance, where two elements are conjoined by "and/or", a first option refers to the applicability of the first element without the second. A second option refers to the applicability of the second element without the first. A third option refers to the applicability of the first and second elements together. Any one of these options is understood to fall within the meaning, and therefore satisfy the requirement of the term "and/or" as used herein. Concurrent applicability of more than one of the options is also understood to fall within the meaning, and therefore satisfy the requirement of the term "and/or" as used herein.

The word "about" as used herein refers to a value being within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. The term "about" is also used to indicate that the amount or value in question may be the value designated or some other value that is approximately the same. The phrase is intended to convey that similar values promote equivalent results or effects according to the invention. In this context "about" may refer to a range above and/or below of up to 10%. The word "about" refers in some embodiments to a range above and below a certain value that is up to 5%, such as up to 2%, up to 1%, or up to 0.5% above or below that value. In one embodiment "about" refers to a range up to 0.1% above and below a given value.

Generally, the present invention relates to all the embodiments described herein as well as to all permutations and combinations thereof. Any particular aspects or embodiments described herein must not be construed as limiting the scope of the present invention on such aspects or embodiments.

The following examples further describe and exemplify the invention provided herein without limiting the invention to any specifications or embodiments defined therein.

EXAMPLES

Example 1

In a semi-batch process acrylonitrile and 2446 g of water were placed in a glass reactor, wherein the acrylonitrile was in each run added such that a concentration of acrylonitrile was reached in the reactor as set out below in Table 1. Then the dried biocatalyst *Rhodococcus rhodochrous*, strain NCIMB 41164 was added to initiate the bioconversion. During the bioconversion further acrylonitrile was added at a controlled rate while the content of acrylonitrile was constantly maintained at the initial value outlined in Table 1. With this respect, the contents of acrylonitrile and acrylamide were measured online during the bioconversion using Fourier Transform Infrared Spectroscopy (FTIR). All in all, 1553 g of acrylonitrile, which is the total amount of acrylonitrile placed in the reactor before starting the bioconversion and added during the reaction, was converted into acrylamide. At the end of the reaction 4 kg of an aqueous acrylamide solution having a content of 52 w/w % acrylamide based on the total weight of the composition in the reactor was obtained.

The following Table 1 shows different runs of the method as described in the preceding paragraph at temperatures of 20° C. and 26° C., respectively, wherein different amounts of the biocatalyst were used and the acrylonitrile content was maintained at different values during the bioconversion.

TABLE 1

| Run | Temperature [° C.] | Amount of biocatalyst [g] | Content of acrylonitrile maintained during the bioconversion [w/w %]* | End of bioconversion [h] | Concentration of acrylic acid at end of bioconversion [ppm]** |
|---|---|---|---|---|---|
| 1 | 20 | 1.3 | 0.5 | 6.7 | 287 |
| 2 | | | 2 | 6.4 | 130 |
| 3 | | 1.47 | 0.5 | 4.9 | 246 |
| 4 | | | 5 | 10.2 | 44 |
| 5 | | 1.84 | 0.5 | 5 | 202 |
| 6 | | | 2 | 3.8 | 154 |
| 7 | | | 2.75 | 2.8 | 80 |
| 8 | | 2.21 | 0.5 | 3.2 | 111 |
| 9 | | | 5 | 2.7 | 59 |
| 10 | 26 | 1.3 | 0.5 | 4.7 | 297 |
| 11 | | | 2 | 5.1 | 206 |
| 12 | | 1.84 | 0.5 | 3.3 | 308 |
| 13 | | | 2 | 2.5 | 164 |
| 14 | | | 2.75 | 2.2 | 68 |
| 15 | | | | 2.2 | 74 |
| 16 | | | | 2.3 | 69 |

*measured online during the bioconversion using Fourier Transform Infrared Spectroscopy (FTIR)
**determined using HPLC according to the method provided below The results outlined in Table 1 show that by maintaining the acrylonitrile content during the bioconversion at 0.3 w/w % or more aqueous acrylamide solutions are produced having low concentrations of acrylic acid. In particular, the results indicate that by increasing the content of acrylonitrile, which is maintained during the bioconversion, the concentration of acrylic acid in the obtained aqueous acrylamide solutions is reduced.

Example 2

The runs of the bioconversion of acrylonitrile to acrylamide were carried out under the same conditions as of Example 1, except:
(i) a higher content of acrylonitrile was maintained from the beginning of the bioconversion for 1 hour;
(ii) after 1 hour from the beginning of the bioconversion the acrylonitrile content was decreased to a lower acrylonitrile content; and
(iii) the lower acrylonitrile content was maintained until the end of the bioconversion, i.e. until conversion of 1553 g acrylonitrile to form 4 kg of an aqueous acrylamide solution having a content of 52 w/w % acrylamide based on the total weight of the composition in the reactor.

The specific conditions and results are shown in Table 2.

TABLE 2

| Run | Temperature [° C.] | Amount of biocatalyst [g] | Content of acrylonitrile maintained during the bioconversion [w/w %]* | End of bioconversion [h] | Concentration of acrylic acid at end of bioconversion [ppm]** |
|---|---|---|---|---|---|
| 1 | 26 | 0.91 | 0.8 (maintained over whole time of the bioconversion) | 5.73 | 482 |
| 2 | | | 1.5 (maintained over 1 hour from beginning of bioconversion), then 0.8 (maintained until end of bioconversion) | 5.94 | 273 |
| 3 | | | 2 (maintained over 1 hour from beginning of bioconversion), then 0.8 (maintained until end of bioconversion) | 5.79 | 202 |

*measured online during the bioconversion using Fourier Transform Infrared Spectroscopy (FTIR)
**determined using HPLC according to the method provided below In run 1 of Table 2 the content of acrylonitrile was maintained at 0.8 w/w % during the whole bioconversion. In runs 2 and 3 a higher content of 1.5 and 2 w/w % of acrylonitrile, respectively, was maintained until one hour from the beginning of the bioconversion. After one hour, the content of acrylonitrile was decreased to 0.8 w/w % and maintained at this value until the end of the bioconversion.

The results show that, at comparable times required until the end of the bioconversion, the concentration of acrylic acid in the obtained aqueous acrylamide solutions is further reduced in case that a higher content of acrylonitrile is maintained over a certain period of time, then the content of acrylonitrile is decreased to a lower content of acrylonitrile and this lower content of acrylonitrile is maintained until the end of the bioconversion.

Example 3

Water and 18 g of acrylonitrile were placed in a reactor. The amount of water was adjusted so that the total amount of water and biocatalyst was 1835 g. Two different forms (i) and (ii) of a biocatalyst were used in independent runs as set forth in the following:
(i) a fermentation broth containing cells of *Rhodococcus rhodochrous*, strain J1 (FERM-BP 1478), with a NHase acticvity of 1512 kU/kg and a water content of 96.1 w/w %; and
(ii) a dry powder obtained by concentration of (i) by centrifugation up to a water content of 83.6 w/w % and then freeze drying of the concentrate. The water content of the dry powder was 13 w/w % and the NHase activity was 211 kU/g.

The biocatalyst was added to the reactor, whereby the reaction started. During the bioconversion 1147 g of additional acrylonitrile was added so that the overall reaction batch size at the end was 3000 g. The temperature was kept constant at 23° C. during the reaction. The content of acrylonitrile was measured online during the bioconversion using Fourier Transform Infrared Spectroscopy (FTIR), and the rate of addition of acrylonitrile was adjusted so that the acrylonitrile content in the reaction mixture was kept constant at 1.0±0.1 w/w % or 0.3 w/w % until the entire acrylonitrile had been added to the reactor. The reaction was stopped after the acrylonitrile content had decreased to <100 ppm due to conversion. At the end of the reaction, the acrylamide concentration in every run was 51 w/w %.

The conditions and results are shown in Table 3 below.

TABLE 3

| Run | Biocatalyst form | Amount of biocatalyst [g] | Content of acrylonitrile maintained during the bioconversion [w/w %]* | Reaction time [h] | Concentration of acrylic acid at end of bioconversion [ppm]** |
|---|---|---|---|---|---|
| 1 | Fermentation broth (i) | 143 | 0.3 | 7.5 | 885 |
| 2 | Fermentation broth (i) | 143 | 1 | 5.7 | 604 |
| 3 | Freeze-dried powder (ii) | 0.92 | 0.3 | 6.6 | 568 |
| 4 | Freeze-dried powder (ii) | 0.92 | 1 | 5.0 | 305 |

*measured online during the bioconversion using Fourier Transform Infrared Spectroscopy (FTIR)
**determined using HPLC according to the method provided below The results of Table 3 show that by using a dried biocatalyst in a bioconversion in which the acrylonitrile content is kept constant the concentration of acrylic acid in the obtained aqueous acrylamide solutions is reduced compared to employing a biocatalyst which has not been subjected to drying.

In the aforementioned examples the concentration of acrylic acid in the obtained aqueous acrylamide solutions was determined using HPLC. The following conditions were applied in order to determine the contents of acrylamide, acrylic acid and acrylonitrile:

Column: Aqua C18, 250*4.6 mm (Phenomenex)
Guard column: C18 Aqua
Temperature: 40° C.
Flow rate: 1.00 ml/min
Injection volume: 1.0 µl
Detection: UV detector, wavelength 210 nm
Stop time: 8.0 minutes
Post time: 0.0 minutes
Maximum pressure: 250 bar
Eluent A: 10 mM $KH_2PO_4$, pH 2.5
Eluent B: Acetonitrile
Gradient:

| Time [min] | A [%] | B [%] | Flow [ml/min] |
|---|---|---|---|
| 0.0 | 90.0 | 10.0 | 1.00 |
| 8.0 | 90.0 | 10.0 | 1.00 |

Matrix: Fermentation broths, bioconversion mixtures
Sample is filtered through 0.22 µm
Analytes:

| | Retention time [min] |
|---|---|
| Acrylamide | 3.29 |
| Acrylic acid | 3.91 |
| Acrylonitrile | 4.35 |

The invention claimed is:

1. A method for preparing an aqueous acrylamide solution, the method comprising:
   (a) adding acrylonitrile, water, and a biocatalyst capable of converting acrylonitrile to acrylamide to a reactor to obtain a composition for bioconversion;
   (b) performing a bioconversion of the acrylonitrile to acrylamide in the reactor; and
   (c) adding further acrylonitrile such that a content of acrylonitrile during the bioconversion is maintained at 0.3 w/w % or more, relative to the total weight of the composition in the reactor, for 10 minutes to 48 hours, wherein the adding of further acrylonitrile comprises:
   (i) maintaining an acrylonitrile content in a first range, which is from 1.2 w/w % to 6 w/w % relative to the total weight of the composition in the reactor, for a first period of time, which is from 30 minutes to 4 hours;
   (ii) decreasing the acrylonitrile content from the first range to a second range, which is from 0.3 w/w % to 1.2 w/w % relative to the total weight of the composition in the reactor; and
   (iii) maintaining an acrylonitrile content in the second range for a second period of time, which is from 30 minutes to 24 hours.

2. The method according to claim 1, wherein an acrylic acid concentration of the composition at the end of the bioconversion is 1500 ppm or less, relative to the total weight of the composition at the end of the bioconversion.

3. The method of claim 1, wherein a weight ratio of the biocatalyst, acrylonitrile and water added during the (a) to (c) is 0.001 to 0.5 w/w % of the biocatalyst, 22 to 45 w/w % of acrylonitrile and a balance to 100 w/w % of water, relative to the total weight (100) w/w %) of the combined weights of the biocatalyst, acrylonitrile and water added during the (a) to (c).

4. The method of claim 1, wherein the bioconversion is performed at a temperature of from 5° C. to 40° C. for 10 minutes to 48 hours.

5. The method of claim 1, wherein the content of acrylonitrile during the bioconversion is maintained at 6 w/w % or less, relative to the total weight of the composition in the reactor.

6. The method of claim 1, wherein
   the first range is from 1.2 w/w % to 4 w/w % relative to the total weight of the composition in the reactor,
   the first period of time is from 30 minutes to 3 hours,
   the second range is from 0.5 w/w % to 1.1 w/w % relative to the total weight of the composition in the reactor, and
   the second period of time is from 30 minutes to 12 hours.

7. The method of claim 6, wherein
   the first range is from 1.3 w/w % to 3 w/w % relative to the total weight of the composition in the reactor,
   the first period of time is from 30 minutes to 2 hours,
   the second range is from 0.6 w/w % to 1.0 w/w % relative to the total weight of the composition in the reactor, and
   the second period of time is from 1 hour to 8 hours.

8. The method of claim 1, wherein the method is carried out using a semi-batch process.

9. The method of claim 1, wherein the content of acrylonitrile is measured using Fourier Transform Infrared Spectroscopy (FTIR).

10. The method of claim 1, wherein the biocatalyst encodes the enzyme nitrile hydratase.

11. The method of claim 1, wherein the biocatalyst is at least one selected from the group consisting of *Rhodococcus, Aspergillus, Acidovorax, Agrobacterium, Bacillus, Bradyrhizobium, Burkholderia, Escherichia, Geobacillus, Klebsiella, Mesorhizobium, Moraxella, Pantoea, Pseudomonas, Rhizobium, Rhodopseudomonas, Serratia, Amycolatopsis, Arthrobacter, Brevibacterium, Corynebacterium, Microbacterium, Micrococcus, Nocardia, Pseudonocardia, Trichoderma, Myrothecium, Aureobasidium, Candida, Cryptococcus, Debaryomyces, Geotrichum, Hanseniaspora, Kluyveromyces, Pichia, Rhodotorula, Comomonas,* and *Pyrococcus*.

12. The method of claim 11, wherein the biocatalyst is at least one selected from the group consisting of *Rhodococcus, Pseudomonas, Escherichia* and *Geobacillus*.

13. The method of claim 1, wherein the biocatalyst is at least one selected from the group consisting of *Rhodococcus rhodochrous, Rhodococcus pyridinovorans, Rhodococcus erythropolis, Rhodococcus equi, Rhodococcus ruber, Rhodococcus opacus, Aspergillus niger, Acidovorax avenae, Acidovorax facilis, Agrobacterium tumefaciens, Agrobacterium radiobacter, Bacillus subtilis, Bacillus pallidus, Bacillus smithii, Bacillus* sp BR449, *Bradyrhizobium oligotrophicum, Bradyrhizobium diazoefficiens, Bradyrhizobium japonicum, Burkholderia cenocepacia, Burkholderia gladioli, Escherichia coli, Geobacillus* sp, RAPc8, *Klebsiella oxytoca, Klebsiella pneumonia, Klebsiella variicola, Mesorhizobium ciceri, Mesorhizobium opportunistum, Mesorhizobium* sp F28, *Moraxella, Pantoea endophytica, Pantoea agglomerans, Pseudomonas chlororaphis, Pseudomonas putida, Rhizobium, Rhodopseudomonas palustris, Serratia liquefaciens, Serratia marcescens, Amycolatopsis, Arthrobacter, Brevibacterium* sp CH1, *Brevibacterium* sp CH2, *Brevibacterium* sp R312, *Brevibacterium imperiale, Brevibacterium casei, Corynebacterium nitrilophilus, Corynebacterium pseudodiphtericicum, Corynebacterium glutamicum, Corynebacterium hoffmanii, Microbacterium imperiale, Microbacterium smegmatis, Micrococcus luteus, Nocardia globerula, Nocardia rhodochrous, Nocardia* sp 163, *Pseudonocardia thermophila, Trichoderma, Myrothecium verrucaria, Aureobasidium pullulans, Candida famata, Candida guilliermondii, Candida tropicalis, Cryptococcus flavus, Cryptococcus* sp UFMG-Y28, *Debaryomyces hanseii, Geotrichum candidum, Geotrichum* sp JR1, *Hanseniaspora*, *Kluyveromyces thermotolerans*, *Pichia kluyveri*, *Rhodotorula glutinis*, *Comomonas testosteroni*, *Pyrococcus abyssi*, *Pyrococcus furiosus*, and *Pyrococcus horikoshii*.

14. The method of claim 13, wherein the biocatalyst is *Rhodococcus rhodochrous*.

15. The method of claim 13, wherein the biocatalyst is *Rhodococcus pyridinovorans*.

16. The method of claim 1, wherein the biocatalyst has been dried before being added to the reactor.

17. The method of claim 16, wherein the biocatalyst has been dried by freeze-drying, spray drying, heat drying, vacuum drying, fluidized bed drying, spray granulation, or a combination thereof.

18. The method of claim 16, wherein the dried biocatalyst is added to the reactor.

19. The method of claim 16, wherein the dried biocatalyst is reconstituted before being added to the reactor.

20. The method of claim 19, wherein the biocatalyst is reconstituted by suspending in an aqueous composition.

21. A method for preparing an aqueous acrylamide solution, the method comprising:
  (a) adding acrylonitrile, water, and a biocatalyst capable of converting acrylonitrile to acrylamide to a reactor to obtain a composition for bioconversion;
  (b) performing a bioconversion of the acrylonitrile to acrylamide in the reactor; and
  (c) adding further acrylonitrile such that a content of acrylonitrile during the bioconversion is maintained at 0.3 w/w % or more until an acrylamide content reaches at least 20 w/w %, relative to the total weight of the composition in the reactor,
  wherein the adding of further acrylonitrile comprises:
  (i) maintaining an acrylonitrile content in a first range, which is from 1.2 w/w % to 6 w/w % relative to the total weight of the composition in the reactor, for a first period of time, which is from 30 minutes to 4 hours;
  (ii) decreasing the acrylonitrile content from the first range to a second range, which is from 0.3 w/w % to 1.2 w/w % relative to the total weight of the composition in the reactor; and
  (iii) maintaining an acrylonitrile content in the second range for a second period of time, which is from 30 minutes to 24 hours.

22. The method of claim 21, wherein
  the first range is from 1.2 w/w % to 4 w/w % relative to the total weight of the composition in the reactor,
  the first period of time is from 30 minutes to 3 hours,
  the second range is from 0.5 w/w % to 1.1 w/w % relative to the total weight of the composition in the reactor, and
  the second period of time is from 30 minutes to 12 hours.

23. The method of claim 22, wherein
  the first range is from 1.3 w/w % to 3 w/w % relative to the total weight of the composition in the reactor,
  the first period of time is from 30 minutes to 2 hours,
  the second range is from 0.6 w/w % to 1.0 w/w % relative to the total weight of the composition in the reactor, and
  the second period of time is from 1 hour to 8 hours.

24. A method for reducing an acrylic acid concentration of an aqueous acrylamide solution prepared by converting acrylonitrile to acrylamide using a biocatalyst, the method comprising:
  (a) adding acrylonitrile, water, and a biocatalyst capable of converting acrylonitrile to acrylamide to a reactor to obtain a composition for bioconversion;
  (b) performing a bioconversion of the acrylonitrile to acrylamide in the reactor; and
  (c) adding further acrylonitrile such that a content of acrylonitrile during the bioconversion is maintained at 0.3 w/w % or more, relative to the total weight of the composition in the reactor,
  wherein the adding of further acrylonitrile comprises:
  (i) maintaining an acrylonitrile content in a first range, which is from 1.2 w/w % to 6 w/w % relative to the total weight of the composition in the reactor, for a first period of time, which is from 30 minutes to 4 hours;
  (ii) decreasing the acrylonitrile content from the first range to a second range, which is from 0.3 w/w % to 1.2 w/w % relative to the total weight of the composition in the reactor; and
  (iii) maintaining an acrylonitrile content in the second range for a second period of time, which is from 30 minutes to 24 hours.

25. The method of claim 24, wherein
  the first range is from 1.2 w/w % to 4 w/w % relative to the total weight of the composition in the reactor,
  the first period of time is from 30 minutes to 3 hours,
  the second range is from 0.5 w/w % to 1.1 w/w % relative to the total weight of the composition in the reactor, and
  the second period of time is from 30 minutes to 12 hours.

26. The method of claim 25, wherein
  the first range is from 1.3 w/w % to 3 w/w % relative to the total weight of the composition in the reactor,
  the first period of time is from 30 minutes to 2 hours,
  the second range is from 0.6 w/w % to 1.0 w/w % relative to the total weight of the composition in the reactor, and
  the second period of time is from 1 hour to 8 hours.

27. A method for preparing an aqueous acrylamide solution, comprising:
  (a) adding acrylonitrile, water, and a biocatalyst capable of converting acrylonitrile to acrylamide to a reactor to obtain a composition for bioconversion;
  (b) performing a bioconversion of the acrylonitrile to acrylamide in the reactor;
  (c) adding further acrylonitrile such that a content of acrylonitrile during the bioconversion is maintained at 0.3 w/w % or more, relative to the total weight of the composition in the reactor; and
  (d) obtaining a composition at the end of the bioconversion, which has an acrylic acid concentration of 1500 ppm or less, relative to the total weight of the composition at the end of the bioconversion,
  wherein the adding of further acrylonitrile comprises:
  (i) maintaining an acrylonitrile content in a first range, which is from 1.2 w/w % to 6 w/w % relative to the total weight of the composition in the reactor, for a first period of time, which is from 30 minutes to 4 hours;
  (ii) decreasing the acrylonitrile content from the first range to a second range, which is from 0.3 w/w % to 1.2 w/w % relative to the total weight of the composition in the reactor; and
  (iii) maintaining an acrylonitrile content in the second range for a second period of time, which is from 30 minutes to 24 hours.

28. The method of claim 27, wherein
  the first range is from 1.2 w/w % to 4 w/w % relative to the total weight of the composition in the reactor,
  the first period of time is from 30 minutes to 3 hours,
  the second range is from 0.5 w/w % to 1.1 w/w % relative to the total weight of the composition in the reactor, and
  the second period of time is from 30 minutes to 12 hours.

29. The method of claim 28, wherein
the first range is from 1.3 w/w % to 3 w/w % relative to the total weight of the composition in the reactor,
the first period of time is from 30 minutes to 2 hours,
the second range is from 0.6 w/w % to 1.0 w/w % relative to the total weight of the composition in the reactor, and
the second period of time is from 1 hour to 8 hours.

\* \* \* \* \*